United States Patent
Quan et al.

(10) Patent No.: US 10,994,111 B2
(45) Date of Patent: May 4, 2021

(54) DRUG-HOLDING MICRONEEDLE ARRAY AND MANUFACTURING METHOD THEREOF

(71) Applicant: COSMED PHARMACEUTICAL CO., LTD., Kyoto (JP)

(72) Inventors: Ying-shu Quan, Kyoto (JP); Fumio Kamiyama, Kyoto (JP); Tomoya Yamada, Kyoto (JP)

(73) Assignee: COSMED PHARMACEUTICAL CO., LTD., Kyoto (JP)

( * ) Notice: Subject to any disclaimer, the term of this patent is extended or adjusted under 35 U.S.C. 154(b) by 0 days.

(21) Appl. No.: 14/767,237

(22) PCT Filed: Feb. 10, 2014

(86) PCT No.: PCT/JP2014/053068
§ 371 (c)(1),
(2) Date: Aug. 11, 2015

(87) PCT Pub. No.: WO2014/126052
PCT Pub. Date: Aug. 21, 2014

(65) Prior Publication Data
US 2016/0001053 A1    Jan. 7, 2016

(30) Foreign Application Priority Data
Feb. 14, 2013    (JP) .............................. JP2013-041194

(51) Int. Cl.
*A61M 37/00* (2006.01)

(52) U.S. Cl.
CPC . *A61M 37/0015* (2013.01); *A61M 2037/0046* (2013.01); *A61M 2037/0053* (2013.01)

(58) Field of Classification Search
CPC ...... A61M 2037/0046; A61M 37/0015; A61M 2037/0023; A61M 2025/0093; A61C 13/00018
(Continued)

(56) References Cited

U.S. PATENT DOCUMENTS 8,883,015 B2 *  11/2014  Kendall ............ A61M 37/0015
                                                              216/11
2010/0280457 A1   11/2010  Tokumoto et al.
(Continued)

FOREIGN PATENT DOCUMENTS

CN    104755128 A    7/2015
JP    2003-238347 A  8/2003
(Continued)

OTHER PUBLICATIONS

International Search Report for Application No. PCT/JP2014/053068 dated May 13, 2014.
(Continued)

*Primary Examiner* — Deanna K Hall
(74) *Attorney, Agent, or Firm* — Cheng Law Group, PLLC

(57) ABSTRACT

The present invention provides a drug-holding microneedle array in which a drug is applied and held only on a tip portion of microneedles for quantitatively holding the drug and for preventing the drug from falling away during insertion of the microneedles.
The drug-holding microneedle array comprises: a microneedle array having a microneedle substrate 4 and microneedles, the microneedles being positioned in plural on the microneedle substrate 4 and a tip portion 1 of the microneedles projecting via steps 2 and a drug held on the tip portion of the microneedles and the steps 2.

11 Claims, 2 Drawing Sheets

(58) Field of Classification Search
USPC .................................................. 604/173
See application file for complete search history.

(56) References Cited

U.S. PATENT DOCUMENTS

| | | | | |
|---|---|---|---|---|
| 2013/0072874 | A1* | 3/2013 | Tokumoto | ......... A61M 37/0015 604/173 |
| 2014/0066842 | A1 | 3/2014 | Zhang et al. | |
| 2015/0290163 | A1 | 10/2015 | Quan et al. | |

FOREIGN PATENT DOCUMENTS

| JP | 2007-89792 | A | | 4/2007 | |
|---|---|---|---|---|---|
| JP | 2007-130417 | A | | 5/2007 | |
| JP | 2007-521090 | A | | 8/2007 | |
| JP | 2007190112 | A | * | 8/2007 | ............ A61M 37/00 |
| JP | 2008-23149 | A | | 2/2008 | |
| JP | 2008-29710 | A | | 2/2008 | |
| JP | 2008-520370 | A | | 6/2008 | |
| JP | 2009-39171 | A | | 2/2009 | |
| JP | 2009-507573 | A | | 2/2009 | |
| JP | 2009-273872 | A | | 11/2009 | |
| JP | 2010-29634 | A | | 2/2010 | |
| JP | 2010-57704 | A | | 3/2010 | |
| JP | 2010-057704 | A | * | 3/2010 | ......... A61M 37/0015 |
| JP | 2010-69270 | A | | 4/2010 | |
| JP | 2011-224308 | A | | 11/2011 | |
| JP | 2011-224332 | A | | 11/2011 | |
| JP | 2012-143423 | A | | 8/2012 | |
| JP | 5298011 | B2 | | 9/2013 | |
| JP | 2013-248299 | A | | 12/2013 | |
| JP | 2013248299 | A | * | 12/2013 | ......... A61M 37/0015 |
| WO | WO-2005/004729 | A1 | | 1/2005 | |
| WO | WO-2006/055799 | A1 | | 5/2006 | |
| WO | WO-2007/030477 | A2 | | 3/2007 | |
| WO | WO-2008/139648 | A1 | | 11/2008 | |
| WO | WO-2012/122162 | A1 | | 9/2012 | |

OTHER PUBLICATIONS

Written Opinion of the International Searching Authority (PCT/ISA/237) for Application No. PCT/JP2014/053068 dated May 13, 2014.
Quay, Ying-shu et al., "The Course of Productization of Microneedle", The Academy of Pharmaceutical Science and Technology, 2009, vol. 69, No. 4, pp. 272-276.
Written Opinion of the International Searching Authority (PCT/ISA/207) for Application No. PCT/JP2014/053068 dated May 13, 2014 (English Translation mailed Aug. 27, 2015).
Quan, Ying-shu et al., "The Course of Productization of Microneedle", The Academy of Pharmaceutical Science and Technology, 2009, vol. 69, No. 4, pp. 272-276.
Supplementary European Search Report for the Application No. EP 14 75 1057 dated Nov. 17, 2016.
Canadian Office Action for the Application No. 2,900,738 dated Dec. 10, 2019.

* cited by examiner

DRUG-HOLDING MICRONEEDLE ARRAY AND MANUFACTURING METHOD THEREOF

TECHNICAL FIELD

The present invention relates to a technique for holding a drug by forming steps on a microneedle to administer the drug quantitatively.

BACKGROUND ART

As a method of administering a drug to a human body, oral, administration and transdermal administration are often used. Injection is a typical transdermal administration method. However, injection is a procedure which takes time and labor of specialists such as physicians and nurses, is painful, and is likely to cause an infection of AIDS, hepatitis B, or the like, so that many people do not welcome the procedure. In contrast, a transdermal administration method without pain using a microneedle array has been recently attracting attention (Non-patent Document 1).

In the transdermal administration of a drug, stratum corneum works as a barrier to drug permeation, so that enough permeability is not always provided by only applying the drug on a skin surface. In contrast, perforation of corneum by using a minute needle, i.e. a microneedle can remarkably improve drug permeation efficiency compared to the application method. An article in which a large number of the microneedles are integrated on a substrate is a microneedle array. In addition, a product in which an adhesive sheet for adhering the microneedle array to a skin, a release sheet for protecting an adhesive surface, and the like are added to the microneedle array to facilitate its use is called a microneedle patch.

Although metals and silicon had been initially used as base materials for the microneedle, various polymer materials have been recently attracting attention in view of their workability. Particularly, when the microneedle is made by using a substance which disappears in a body by metabolism, such as saccharide, as the base material, no accident occurs even if the needle is broken and remains in a skin.

When the base material for microneedle is saccharide, if the microneedle is made by adding a drug into the saccharide, the drug can be easily administered into and under a skin through dissolving the inserted microneedle in a body (Patent Document 1). Particularly, when a microneedle made of a biosoluble polymer substance such as hyaluronic acid or collagen is applied to a skin, moisture in the skin diffuses in a needle portion, so the needle portion inserted into the skin swells and then is dissolved. By the diffusion of hyaluronic acid or collagen into the skin due to the dissolution of the needle portion, an antiwrinkle action is expressed, or otherwise the drug and a valuable substance previously dissolved in the needle portion are diffused in the skin (Patent Documents 2 and 3).

However, some drugs to be contained in the microneedle array are extremely expensive, or can be obtained only in minute amounts. When such an expensive and valuable drug is contained in the base material to make the microneedle array, the drug would be contained not only in its microneedle portion but also in its substrate portion. When this microneedle array is inserted into a skin, the drug contained in the microneedle portion is incorporated and diffused in a body, but the drug remaining in the substrate portion is discarded without utilization, resulting in low usage efficiency of the expensive drug.

Some trials for efficient utilization of the expensive drug are already known. A method in which surfaces of the microneedles are coated with a drug by using a drug solution (Patent Documents 4 to 7) and a method in which a granulated drug is converged to tips of microneedles by centrifugation while the microneedles maintain softness (Patent Document 8) have been reported. The method of coating the surfaces of microneedles with a drug and the method of adhering a drug to the tips of microneedles from a drug solution have a problem that the drug must be heated or that the adhered drug falls away during insertion of the microneedles. In contrast, a method in which an adhered drug and a microneedle body were integrated by dissolving the drug in a solvent of the microneedle material to prevent the adhered drug from falling away was proposed (Patent Document 9).

The method of soaking the tips of microneedles into a drug solution to adhere the drug to the tips of microneedles is easily put into practical use due to its convenience (Patent Documents 4 to 7, 9). However, it is very difficult to quantitatively apply the drug to the tips of microneedles with little unevenness.

In case of a microneedle made of a hydrophobic material, it is difficult to apply a drug from an aqueous solution itself, so quantitative loading with the drug is impossible. When a microneedle made of as hydrophilic material is only soaked into a drug aqueous solution, it is impossible to quantitatively load the tip portion of microneedles with the drug since the drug aqueous solution is moved up from a bottom of the needle to a substrate portion by capillary phenomenon to widely distribute the drug. Several hundred microneedles stand closely With intervals of 20 μm to 1,000 μm in one microneedle array, so the drug aqueous solution is extremely easily moved up by capillary phenomenon. Thus, although several trials have been repeated, it is extremely difficult that the microneedle array is soaked into the drug aqueous solution to a fixed depth to quantitatively hold the drug.

In order to prevent the capillary phenomenon, a method of masking any place other than the tip portion of microneedles before applying a drug has been proposed (Patent Document 5). A method of feeding a drug into a large number of holes with a spatula and then inserting the microneedles into the holes to enhance the quantitativity of a drug adhesion amount (Patent Document 7) has been also proposed. However, since execution of these methods is very complicated and furthermore technique for preventing the drug from falling away during insertion of the microneedles into a skin is not shown, the methods are considered to be insufficient for the quantitative administration of the drug.

The microneedle array made of the biosoluble polymer substance is often manufactured by using a mold (Patent Document 2). A microneedle pattern is formed by lithography using a photosensitive resin, and then transferred to make a mold with concave portions for forming the microneedles. A microneedle material may be casted onto this mold, subsequently heated to vaporize moisture, and then the solidified material may be removed from the mold to obtain the microneedle array.

For making the microneedles with a polymer suitable for injection molding, cuts corresponding to a shape of the microneedles are made onto a metal mold by fine metal-working, and then the microneedles can be made with a commercially available injection molding machine. A method of manufacturing the microneedles with unevenness and a plurality of steps in this manner has been already proposed (Patent Documents 10, 11).

PRIOR ART

Patent Documents

[Patent Document 1] JP-2003238347A (Tobinaga)
[Patent Document 2] JP-2009273872A (CosMED)
[Patent Document 3] JP-2010029634A (CosMED)
[Patent Document 4] JP-2008029710 A (HAMAMATSU)
[Patent Document 5] JP-2007521090A (Alza)
[Patent Document 6] JP-2008520370A (3M)
[Patent Document 7] WO-2008139648A1 (HISAMITSU)
[Patent Document 8] JP-2009507573A (KWON)
[Patent Document 9] JP-2011224308A (CosMED)
[Patent Document 10] JP-2005023149A (TOPPAN)
[Patent Document 11] JP-2009039171A (DAIICHI KASEI)

Non-Patent Documents

[Non-Patent Document 1] Ying-Shu QUAN, Fumio KAMIYAMA "The Course of Productization of Microneedle", The Academy of Pharmaceutical Science and Technology, Japan; July 2009, Vol. 69, 4th issue, p. 272-276

SUMMARY OF INVENTION

Technical Problem

As a method of holding a drug on the microneedle, it is principally easy to apply the drug to the tips of microneedles by soaking the tips of microneedles into a drug solution. However, in this method, the drug solution (an aqueous solution is assumed) is moved up along a periphery of the microneedle by capillary phenomenon, so quantitative loading with the drug is extremely difficult. In addition, there is a drawback that the drug falls away during insertion of the microneedles. A new method for overcoming these drawbacks is demanded.

Solution to Problem

A drug-holding microneedle array according to the present invention made for solving the above-mentioned problem is characterized by comprising:
a microneedle array having a microneedle substrate and microneedles, the microneedles being positioned in plural on the microneedle substrate and a tip portion of microneedles projecting via steps; and
a drug held on the tip portion and the steps of the microneedles.
"Tip portion" as used herein means the entire portion projecting from the above-mentioned steps towards a tip.

When the steps are formed in the microneedles, even if a drug aqueous solution is moved up by capillary phenomenon, it stops at the steps and is no longer moved up. Thereby, the drug can be held quantitatively.

When the microneedles have no step, is impossible to quantitatively hold the drug only on the tip portion of microneedles since the drug aqueous solution is moved up along the microneedle to the substrate portion by capillary phenomenon and thus even the substrate is wet.

In addition, the drug held on the tip portion and the steps of the microneedles is supported by the steps, so the drug does not fall away during insertion of the microneedles into a skin and is quantitatively delivered into the skin by the insertion of the microneedles.

"Step" as used herein means a portion where a cross section area of the microneedle is reduced discontinuously from a certain point on the microneedle toward the tip and where a cross section presents a step-wise shape as shown in FIG. 1.

It is conceivable that, instead of the steps, a recess or a groove is formed in the microneedle to hold a drug. However, it is very difficult to mass-produce the microneedles by making a mold for such a microneedle.

"Drug" as used herein includes all compounds which work on a skin or penetrate a skin to express any beneficial action. Examples of a drug suitable for the object of the present invention include, for example, bioactive peptides and derivatives thereof, nucleic acids, oligonucleotides, various antigen proteins, bacteria, virus fragments, and the like.

The above-mentioned bioactive peptides and the derivatives thereof include, for example, calcitonin, adrenocorticotropic hormone, parathyroid hormone (PTH), hPTH (1→34), insulin, exeudin, secretin, oxytocin, angiotensin, β-endorphin, glucagon, vasopressin, somatostatin, gastrin, luteinizing hormone-releasing hormone, enkephalin, neurotensin, atrial natriuretic peptide, growth hormone, growth hormone-releasing hormone, bradykinin, substance P, dynorphin, thyroid stimulating hormone, prolactin, interferons, interleukins, G-CSF, glutathione peroxidase, superoxide dismutase, desmopressin, somatomedin, endothelin, salts thereof, and the like. The antigen proteins include influenza virus antigen, HBs surface antigen, HBe antigen, and the like. The drug may be a cosmetic.

As base materials for the microneedle, metals, plastics, silicon, or the like can be used other than water-soluble polymers or biodegradable polymers. Practically, the water-soluble polymers which can be mass-produced by casting onto the metal mold, or polymers which are injection-moldable or press-moldable can be preferably used as the base materials. Examples of the water-soluble polymers include hyaluronic acid, sodium chondroitin sulfate, carboxymethyl cellulose sodium salt, hydroxypropyl cellulose, dextran, and mixtures thereof. Examples of the polymers which are easily injection-moldable or press-moldable include nylon, polycarbonate, polylactic acid, copolymer of lactic acid and glycolic acid, polyglycolic acid, polyethylene terephthalate, COP (cyclic olefin polymer), and mixtures thereof.

A manufacturing method of the drug-holding microneedle array according to the present invention comprises processes of:
preparing a microneedle array having a microneedle substrate and microneedles, the microneedles being positioned in plural on the microneedle substrate and a tip portion of the microneedles projecting via steps;
soaking the tip portion of the microneedles into a drug aqueous solution; and
pulling up the tip portion of the microneedles from the drug aqueous solution and drying in order to hold a drug on the tip portion of the microneedles so that a drug administration amount is quantitatively fixed.

When soaking the tips of microneedles into the drug aqueous solution to hold the drug on the tips of microneedles, it is desirable that a coexistent substance is added into the drug aqueous solution and dissolved to hold the drug on the microneedles with the coexistent substance in drying after application. Namely, in the microneedle array according to the present invention, it is preferable that a water-soluble polymer or a mixture of the water-soluble polymer and low molecular weight saccharides which is the coexistent substance is added to the above-mentioned drug.

As the coexistent substance, a substance which does not lose stability of the drug is preferable, and, for example, the water-soluble polymer substance such as hyaluronic acid, collagen, dextrin, dextran, sodium chondroitin sulfate, hydroxypropyl cellulose, ethyl cellulose, carboxymethyl cellulose sodium salt, and alginic acid; the low molecular weight saccharides such as glucose, sucrose, maltose, and trehalose; or mixtures thereof are suitable.

If the coexistent substance is only the water-soluble polymer substance, a dissolution time of a coating in a skin at transdermal administration of the microneedles may be long. In contrast, a coating made of only the low molecular weight saccharides may have insufficient mechanical strength. Thus, as the coexistent substance added to the drug aqueous solution into which the microneedles are soaked, the mixture of the water-soluble polymer and the low molecular weight saccharides is desirable. In such case, a ratio of the low molecular weight saccharides to a total weight of the coexistent substance is desirably 80% by weight or less.

A concentration of the coexistent substance in the drug aqueous solution is desirably 2% to 50%. If the concentration is less than 2%, viscosity of the drug aqueous solution is low, so a coating adhesion amount in soaking may be small. In contrast, if the concentration is more than 50%, since the concentration in the drug aqueous solution is too high, drug application may not be stable.

To the drug aqueous solution, an antioxidant, a surfactant, and the like may be added as required.

The microneedle array can be mass-produced by using a mold (metal mold). The microneedles made of the water-soluble polymer material may be mass-produced by casting a material aqueous solution onto the mold and removing the material after drying (Patent Document 2: [0031] to [0033]).

The microneedles made of the injection-moldable polymer material may be manufactured by injection-molding the material with a metal mold (Patent Document 1: [0017], [0018]). For the metal mold for injection molding, stainless steel, heat resistant steel, superalloy, and the like can be used. A typical metal mold has cut portions corresponding to 100 to 900 microneedles per 1 $cm^2$ to make a shape of the microneedles. Fine working means such as grinder can be used to make the cut portions.

In the present invention, the shape of the microneedles is not particularly limited, and, for example, cone-shaped microneedles can be used. Total length of the microneedle (a tip portion 1+a root portion 3 in FIG. 1) is preferably around 70 to 1000 μm, and is more preferably 150 to 800 μm. FIG. 1 illustrates a schematic cross-sectional view, and the numbers correspond to the arrows in FIG. 1. FIG. 1 shows one microneedle extracted from a plurality of microneedles which are positioned on the above-mentioned microneedle substrate 4. The microneedle array according to the present invention has the microneedle substrate 4 and the microneedles, which are positioned in plural on the above-mentioned microneedle substrate 4 and has the tip portion 1 projecting via steps 2. The microneedle has the tip portion 1, the root portion 3, and the steps 2.

In the microneedle with steps, it is preferable that length of the tip portion 1 is 50 to 500 μm and that the rest of the microneedle is the root portion 3. It is more preferable that the tip portion 1 is 50 to 300 μm within the total length of 150 to 800 μm and that the rest of the microneedle is the root portion 3. A size of edges of the steps 2 between the tip portion 1 and the root portion 3 is preferably more than 10 μm and less than 100 μm, and is more preferably more than 14 μm and less than 50 μm. If the edges of the steps 2 are less than 10 μm, it may be unsuitable for the object of the present invention of preventing the drug solution from being moved up by capillary phenomenon and of increasing application strength. In contrast, if the edges of the steps 2 are 100 μm or more a shock to a skin in inserting the microneedle into the skin may be large.

The edges of the steps 2 mean surfaces orthogonal to an axis of the microneedle (surfaces parallel to the substrate 4), within a range of working accuracy. Furthermore, the size of the edges of the steps 2 means radial difference between the tip portion 1 and the root portion 3 at the steps. The root portion 3 is not necessarily cone-shaped, but may be cylinder-shaped.

Advantageous Effects of Invention

The microneedle with steps has the following two remarkable effects compared to the microneedle without step.

(1) A drug holding amount can be quantitative. When the tip portion is soaked into a drug solution to adhere a drug, the effect of capillary phenomenon can be overcome by forming the steps, so an amount of the drug held on the tip portion is fixed.

(2) The drug does not fall away during insertion of the microneedles into a skin, so usage efficiency of the drug is high and an administration amount is fixed.

Namely, by forming the steps in the microneedle, a simple manufacturing process in which the microneedle is soaked into a drug solution to adhere a drug allows to make the microneedle which can quantitatively administer a necessary amount of the drug.

DESCRIPTION OF EMBODIMENTS

Although examples of the present invention are described below, the present invention is not limited to the examples.

Although, in all the examples of the present invention, cone-shaped microneedles are used, it is clear that the examples can be also applied to a microneedle which is not cone-shaped, such as quadrangular pyramid or triangular pyramid and that steps are effective in such cases.

For microneedles with steps or without step made of injection-moldable materials in the present examples, a metal mold with cavities for molding into a microneedle array was made by using an alloy tool steel, and then the metal mold was set to an injection molding machine manufactured by Fanuc Corporation to injection mold at an injection temperature of 250° C.

Example 1

Figure 1:
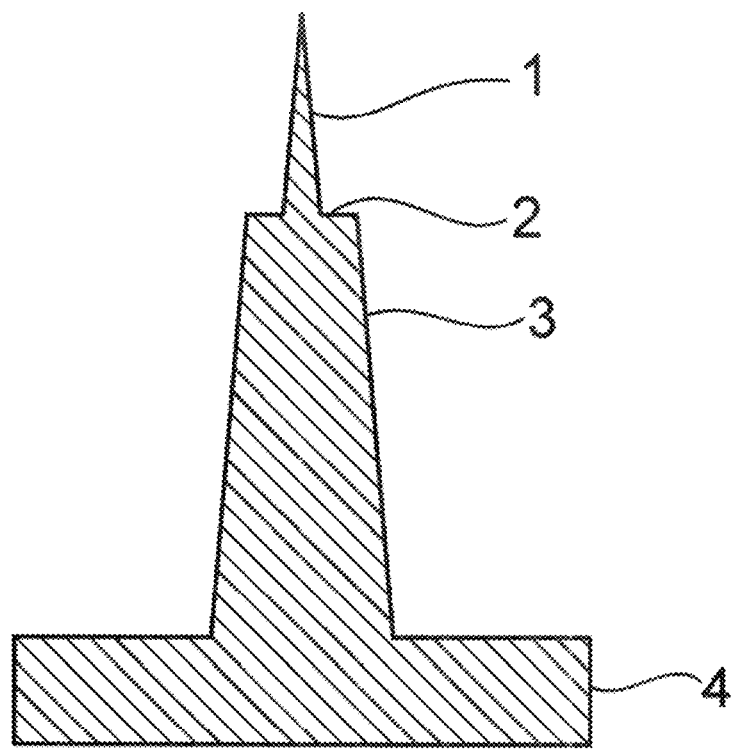
FIG. 1 is a schematic cross-sectional view of one microneedle with step extracted from a plurality of microneedles which are positioned in the microneedle array according to the present invention.

By using Nylon 12 as base materials, a microneedle array comprising the microneedles with steps and a microneedle array comprising the microneedles without steps were manufactured by the injection molding method. FIG. 1 shows structure of one microneedle with steps extracted from a plurality of microneedles which are positioned in the microneedle array. In the figure, 1 is a tip portion, 2 is a step, 3 is a root portion, and 4 is a substrate. Length of the tip portion is 200 μm, length of the root portion is 430 μm, a size of edges of the steps is 30 μm, and an interval between the needles is 400 μm.

Portions up to 100 μm from tips of the tip portions of microneedles in both the microneedle arrays (1 cm in diameter) were soaked into an aqueous solution of hyaluronic acid (FCH-80LE manbiochemif Co., Ltd.) and blue pigment (blue No. 1, Nacalai Tesque Co., Ltd.). The blue pigment was used as a substitution to a drug, and was selected to easily observe an adhesion state of the drug with a microscope.

Figure 2:
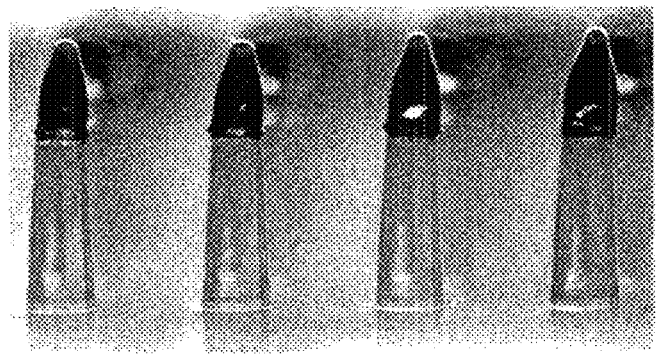
FIG. 2 is a photograph of microneedles with steps of Example 1 to which hyaluronic acid containing blue pigment is applied and adhered.

In the case of the microneedles with steps, when 100 μm from the tips of the tip portions are soaked, the drug is adhered to positions of the steps (200 μm) by capillary phenomenon. In the case of the microneedles without step, the drug reaches the substrate. This is because a surface of nylon is hydrophilic and thus the aqueous solution is moved up by capillary phenomenon. Each microneedle was pulled up and dried to manufacture the microneedle arrays comprising the microneedles in which the mixture of hyaluronic acid and blue pigment was applied to the tip portions. FIG. 2 is a photograph of the microneedles with steps to which hyaluronic acid containing blue pigment was adhered. Since the figure is a black-and-white photograph, portions looking black in the figure are blue, so it is clearly shown that the drug is held on the steps.

The tip portions of microneedles in both the microneedle arrays were inserted into laminated Parafilms (1 mm thickness) and were drawn out immediately. The laminated Parafilm was used as a skin model. Then, the Parafilm was soaked into 1.0 mL of water to extract the blue pigment, and absorbancy of a solution at a wavelength of 628 nm was measured. The absorbancy values of the extract solution from the microneedles with steps and the extract solution from the microneedles without steps were 0.002 and 0.016, respectively. This indicates that, in the microneedles without step, the drug applied to the tip portions of the microneedles easily falls away during the insertion into the Parafilm. On the other hand, in the microneedles with steps, the blue pigment was hardly adhered to the Parafilm, and remained on the microneedles after the insertion into the Parafilm.

This result indicates that a drug less often falls away during insertion when the steps are formed in the microneedle. This is considered to be because the steps serve to protect the drug.

Example 2

Figure 3:
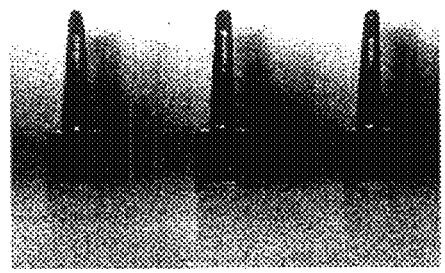
FIG. 3 is a photograph of microneedles with steps of Example 2 before applying a drug.

From Nylon 12 (L1640 Daicel Degussa Co., Ltd.) as a raw material, a microneedle array with steps was made by injection molding. For microneedles, length of a tip portion was 270 μm, an upper diameter of the tip portion was 20 μm, a lower diameter of the tip portion was 60 μm, length of a root portion was 160 μm, a lower diameter of the root portion was 140 μm, an upper diameter of the root portion was 130 μm, a size of edges was 35 μm, and an interval between the needles was 400 μm. "Upper" and "lower" are based on a state that the tip portion is above and that the root portion is below. A diameter of the microneedle array was 1 cm. FIG. 3 shows a microscope photograph of the molded microneedles. Furthermore, microneedles with steps, in which a size of a tip portion and an interval between the needles was the same and a size of a root portion and a size of edges were changed to 50 and 100 μm, were also made.

Effectiveness of the steps was evaluated by varying the size of the edges of the steps.

For microneedles in which the size of the edges of the steps was less than 35 μm, the tip portions of microneedles were made thicker by the following method. The tip portions of the microneedle array with steps in which the size or the edges of the steps was 35 μm were soaked into 1% acetone solution of a cyanoacrylate adhesive (Cemedine Co., Ltd.), and then the soak was further repeated while measuring the size after drying to make five kinds of microneedles with steps which were different in size from each other. In this case, flatness of the edges of the steps was maintained. The sizes of the edges of five kinds of the steps measured with a stereomicroscope (Leica M205C, Leica microsystems Co., Ltd.) were 21, 14, 10, 5, and 0 μm.

Portions up to 90 μm from tips of the tip portions of microneedles were soaked into an aqueous solution containing 2% of hydroxypropyl cellulose (HPC-L Nippon Soda Co., Ltd) and 0.2% of blue pigment (blue No. 1, Nacalai Tesque Co., Ltd.). Each microneedle was pulled up and dried before resoaking and drying, and then adhesion states of the blue pigment to the tip portions of needles were observed with the stereomicroscope. Results are summarized in Table 1.

TABLE I

| Microneedles No. | Edge size (μm) | Adhesion state of blue pigment |
| --- | --- | --- |
| 1 | 100 | Blue pigment reached the steps and is held only on the tip portion |
| 2 | 50 | Same as above |
| 3 | 35 | Same as above |
| 4 | 21 | Same as above |
| 5 | 14 | Same as above |
| 6 | 10 | A part of blue pigment is over the steps to move upward a little |
| 7 | 5 | Blue pigment is over the steps to reach the substrate |
| 8 | 0 | Same as above |

Even if only the tips of the tip portions are soaked into the aqueous solution of the blue pigment, the aqueous solution is moved up along side surfaces of the microneedles by capillary phenomenon and reaches the edges of the steps. When the size of the edges of the steps is 14 μm or more, the aqueous solution stops at the edges. It is revealed that, when the size of the edges of the steps is 10 μm, a part of the aqueous solution is over the steps, and that, when the size of the edges of the steps is 5 μm, the aqueous solution is further moved up over the steps. From the results of this table, it can be concluded that the size of the edges of the steps is preferably more than 10 μm. Furthermore, it can be concluded that the size is more preferably more than 14 μm.

Example 3

From polyglycolic acid (Kuredux, kureha Co., Ltd.) as a raw material, by injection molding under similar conditions to Example 2 except that the injection temperature was 260° C., microneedles with steps in which a size of edges of the steps was 35 μm were obtained. 90 μm of tip portions of the microneedles were soaked into an aqueous solution containing 10% of hydroxypropyl cellulose (HPC-L Soda Co., Ltd.) and 0.1 of red pigment (red No. 102, Nacalai Tesque Co., Ltd.). The microneedles were pulled up and dried before resoaking and drying, and then applied states of the red pigment to the tip portions of needles were observed with the stereomicroscope. Through the observation, the red pigment appeared to stop at the step portions.

This result indicates that the results of Example 2 are not specific to the blue pigment.

Example 4

The tip portions of the microneedles with steps made in the same way as Example 2 were soaked into an aqueous solution containing insulin. For the aqueous solution containing insulin, bovine insulin (Nacalai Tesque Co., Ltd.) was dissolved in an aqueous solution of hydrochloric acid with pH 2.5, and then the resultant solution was added to an aqueous solution containing 10% of hydroxypropyl cellulose (HPC-L, Nippon Soda Co., Ltd.). An insulin concentration was 1.0 unit/mL. The portions up to 90 μm from the tips of the tip portions of microneedles were soaked into the aqueous solution of insulin, pulled up and dried before resoaking, so the portions were soaked four times. Through microscopical observation of the obtained microneedle array, hydroxypropyl cellulose appeared to stop at the steps. This result also indicates that the results of Example 2 are not specific to the blue pigment.

This experiment was carried out five times to measure Unevenness of amounts of insulin which was adhered to the tip portions of five microneedle arrays. In the measurement of the amount of insulin, Grazyme insulin-EIA TEST kit (Wako Pure Chemical Industries, Ltd.) was utilized. An average amount of insulin per one microneedle array was 0.18 unit, and the unevenness was within 15% CV.

Example 5

A microneedle array was molded with COP polymer (1020R, Nippon Zeon Co., Ltd.) under the same conditions as Example 2. Microneedles with steps, in which a size of edges of the steps is 35 μm, are expressed as microneedles 9 in Table 2. Also, a cone-shaped microneedle array in which length was 300 μm, a diameter of a tip portion was 20 μm, a lower diameter was 70 μm, and an interval between needles was 400 μm was molded. The microneedles are expressed as microneedles 10 in Table 2. A diameter of both the microneedle arrays was 1 cm.

Portions up to 90 μm from tips of the tip portions of the microneedle array in which the size of the edges of the steps was 35 μm were soaked into an aqueous solution containing 20% of hydroxypropyl cellulose (HPC-L, Nippon Soda. Co., Ltd.) and 0.1% of red pigment (red No. 102, Nacalai Tesque Co., Ltd). The microneedles were pulled up and dried before resoaking, and then the portions were soaked and dried three times. Since, in the microneedle array without steps, liquid had reached a substrate portion through a one-time soak under the same conditions, the soak was finished at the one time and then the soaked portions were dried.

The obtained microneedle arrays were soaked into 1 mL of purified water to dissolve the red pigment and then absorbancy at 507 μm was measured. The test was carried out on each microneedle array three times. The following table shows the results.

TABLE 2

|  | Edge size (μm) | Absorbancy of red pigment |
|---|---|---|
| Microneedles 9 | 35 | 0.058 |
|  |  | 0.049 |
|  |  | 0.051 |
| Microneedles 10 | 0 (No step) | 1.293 |
|  |  | 0.753 |
|  |  | 1.043 |

Figure 4:
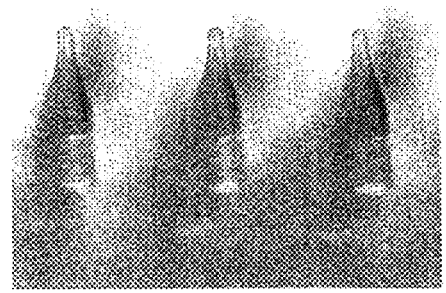
FIG. 4 is a photograph of microneedles with steps of Example 5 after adhering a drug.
Figure 5:
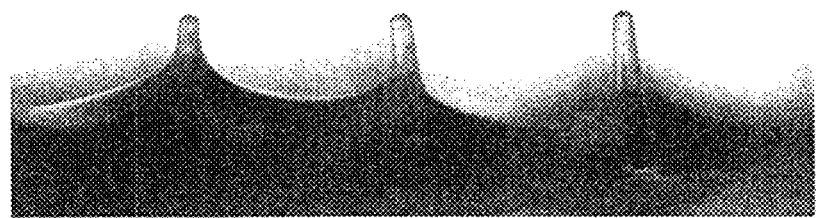
FIG. 5 is photograph of microneedles without step of Example 5 after adhering the drug.

In the microneedles with steps, as shown in FIG. 4, the red pigment is adhered to only the tip portions of needles, and unevenness of adhesion amounts between the microneedles is little. Namely, the adhesion amount can be quantitative by forming the steps. In contrast, in the microneedles without steps, as shown in FIG. 5, even the substrate portion of the microneedles is soaked into the solution of the red pigment, so the adhesion amount of the red pigment is large and the unevenness of the adhesion amounts is also large. Namely, it is shown that, when the steps are not formed, the adhesion amount is not quantitative. Since the drawings are displayed in black-and-white, although red portions are not clear in FIGS. 4 and 5, slightly deep color portions are colored with the red pigment. In color photographs, the tip portions in FIG. 4 and the entire microneedle array in FIG. 5 are colored red. FIG. 5 shows that even the substrate is colored red.

Example 6

From polyglycolic acid (Kuredux, kureha Co., Ltd.) as a raw material, by injection molding under similar conditions to Example 2 except that the injection temperature was 260° C., microneedles with steps in which a size of edges was 35 μm were obtained.

Composition of an aqueous solution into which the microneedles were soaked was varied to examine effectiveness of coexistent substances. Table 3 shows water-soluble polymers used in the solution and composition of the coexistent substance. Although a drug or a model drug is not contained in the aqueous solution, it is clear that the test results are applied to an aqueous solution containing the drug.

Under similar conditions to Example 4, tips of the microneedles were soaked into aqueous solutions containing the coexistent substances. The microneedle array in which solid contents had been adhered to the needles after drying, was applied to an upper arm of four volunteers and then removed after 5 minutes to evaluate whether adhered substances were dissolved into a skin through microscopical observation.

Whether the dissolution was "complete dissolution" or "incomplete dissolution" was judged through the observation, and ratios of persons who evaluated to be complete dissolution in the four volunteers are shown in Table 3 as evaluation results. In Table 3, for example, three-quarters means that three of the four volunteers evaluated to be complete dissolution. "Complete dissolution" means that the adhered substances completely disappear on the needles after the application to the skin, and "incomplete dissolution" means that the adhered substances partially remain on the needles.

TABLE 3

| | Amount of water-soluble polymer and coexistent substance in solution for soaking | | |
|---|---|---|---|
| | Water-soluble polymer | Coexistent substance | Evaluation result |
| Coexistent substance 1 | hyaluronic acid 10% | None | 1/4 |
| Coexistent substance 2 | hyaluronic acid 8% | glucose 2% | 4/4 |
| Coexistent substance 3 | hydroxypropylcellulose 20% | None | 2/4 |
| Coexistent substance 4 | hydroxypropylcellulose 10% | trehalose 30% | 4/4 |

The results in Table 3 show that a mixture of a water-soluble polymer and low molecular weight saccharides is desirable for the coexistent substance of a drug aqueous solution into which microneedles are soaked. When the low molecular weight saccharides do not coexist, the adhered substance is not completely dissolved in five minutes.

Example 7

Microneedles were made with a water-soluble polymer as base materials. First, molds for forming the microneedles were made by lithography. Microneedle patterns in a predetermined shape were formed by light-irradiating photosensitive resins, and then concave portions for forming the microneedles to which the microneedle patterns in the predetermined shape were transferred through electro-casting were formed as the molds. The molds were filled with an aqueous solution containing 5% of hyaluronic acid (molecular weight 800,000, Trade Name: FCH-80LE, Kikkoman Biochemifa Co., Ltd.) under room temperature, and then, after vaporizing moisture and drying, the solidified materials were removed to make microneedle arrays. Three kinds of microneedles with different needle sizes were made, and the microneedle arrays were cut into a circle with a diameter of 1 cm. An interval between the needles was 400 µm. Table 4 shows sizes of microneedles 11, 12, and 13. "Upper" and "lower" are based on a state that the tip portion is above and that the root portion is below.

TABLE 4

| | Tip portion (µm) | | | Root portion (µm) | | | Edge |
|---|---|---|---|---|---|---|---|
| Microneedles No. | Upper diameter | Lower diameter | Length | Upper diameter | Lower diameter | Length | size (µm) |
| 11 | 20 | 60 | 280 | 260 | 300 | 150 | 100 |
| 12 | 20 | 60 | 280 | 160 | 180 | 150 | 50 |
| 13 | 20 | 60 | 280 | 130 | 150 | 150 | 35 |

Portions up to 90 µm from tips of the tip portions of the microneedle arrays made as mentioned above, in which the sizes of the edges of the steps were 35, 50, and 100 µm, were soaked into an aqueous solution containing 20% of hydroxypropyl cellulose (HPC-L, Nippon Soda Co., Ltd.) and 0.1% of ovalbumin (Nacalai Tesque Co., Ltd.) as a model drug, and were pulled up immediately and dried before subjected to a test.

By using the three kinds of microneedle arrays with the model drug loaded on the tips, the model drug was administered to extracted pig skins (purchased from CHARLES RIVER LABORATORIES JAPAN, INC). The three kinds of microneedle arrays were transdermally-administered with a spring-type applicator, and were removed after one hour. Through observation of the microneedle arrays-administered portions of the pig skins with the stereomicroscope, dotted needle insertion marks could be observed at the administered portions of the skins in all of the three kinds of application, so the tip portions of needles had been surely inserted into the skin.

Through observation of the removed microneedle arrays with the stereomicroscope, the tip portions appeared to be completely dissolved in all of the three kinds of application. The root portions of the microneedles 13 appeared to be completely dissolved. The root portions of the microneedles 12 also appeared to be almost dissolved. However, the root portions of the microneedles 11 appeared to be incompletely dissolved. It is conceivable that, when the size of the edges is large, the edges of the steps interfere with the insertion into the skin. It is conceivable that, in the microneedles 11 with the large edges of the steps, since the root portions of the microneedles were not inserted into the skin, the root portions could not be dissolved. Thus, it can be concluded that the size of the edges of the steps is desirably 100 µm or less, and is more desirably 50 µm or less. It is conceivable that, owing to moisture supply from the skin, the root portions were somewhat dissolved even when the edges of the steps were large.

REFERENCE NUMERALS 1 tip portion
2 step
3 root portion
4 substrate

The invention claimed is:
1. A drug-holding microneedle array comprising:
   a microneedle array having a microneedle substrate and microneedles, the microneedles being positioned in plural on the microneedle substrate, each microneedle comprising a tip portion projecting from a root portion via a step that narrows a width of the microneedle from the root portion to the tip portion, the step being arranged at a plane where the tip portion meets the root portion; and
   a drug held on the tip portions and the steps of the microneedles,
   wherein a first width is defined as a distance along the plane where the tip portion meets the root portion from a center of the microneedle to an outer edge of the tip portion,
   a second width is defined as a distance along the plane where the tip portion meets the root portion from the center of the microneedle to an outer edge of the root portion,
   a difference between the first width and the second width is more than 14 µm and less than 100 µm, and
   the tip portion is cone-shaped.

2. The drug-holding microneedle array according to claim 1, wherein the difference between the first width and the second width is less than 50 µm.

3. The drug-holding microneedle array according to claim 1, wherein a base material of the microneedles is polymers which are injection-moldable or press-moldable.

4. The drug-holding microneedle array according to claim 1, wherein a base material of the microneedles is at least one selected from a group consisting of nylon, polycarbonate, polylactic acid, copolymer of lactic acid and glycolic acid, polyglycolic acid, polyethylene terephthalate, and cyclic olefin polymer.

5. The drug-holding microneedle array according to claim 1, wherein a base material of the microneedles is water-soluble polymers.

6. The drug-holding microneedle array according to claim 5, wherein the base materials of the microneedles is at least one selected from a group consisting of hyaluronic acid, sodium chondroitin sulfate, carboxymethyl cellulose sodium salt, hydroxypropyl cellulose, and dextran.

7. The drug-holding microneedle array according to claim 1, wherein the drug is added with a water-soluble polymer or a mixture of the water-soluble polymer and low molecular weight saccharides.

8. The drug-holding microneedle array according to claim 7, wherein the water-soluble polymer is at least one selected from a group consisting of hyaluronic acid, collagen, dextrin, dextran, sodium chondroitin sulfate, carboxymethyl cellulose sodium salt, hydroxypropyl cellulose, and ethyl cellulose.

9. The drug-holding microneedle array according to claim 7, wherein the low molecular weight saccharides are at least one selected from a group consisting of glucose, sucrose, maltose, and trehalose.

10. The drug-holding microneedle array according to claim 1, wherein the microneedles are cone-shaped microneedles.

11. The drug-holding microneedle array according to claim 1, wherein the root portion is one of cylinder-shaped and truncated cone-shaped.

\* \* \* \* \*